United States Patent [19]

Broecker et al.

[11] Patent Number: 4,638,085
[45] Date of Patent: Jan. 20, 1987

[54] PREPARATION OF METHYL METHACRYLATE FROM METHACROLEIN

[75] Inventors: Franz J. Broecker, Ludwigshafen; Gerd Duembgen, Dannstadt-Schauernheim; Gerd Fouquet, Neustadt; Richard Krabetz, Kirchheim; Franz Merger, Frankenthal; Friedbert Nees, Stutensee, all of Fed. Rep. of Germany

[73] Assignee: BASF Aktiengesellschaft, Ludwigshafen, Fed. Rep. of Germany

[21] Appl. No.: 660,978

[22] Filed: Nov. 21, 1984

Related U.S. Application Data

[63] Continuation of Ser. No. 473,601, Mar. 9, 1983, abandoned.

[30] Foreign Application Priority Data

Mar. 24, 1982 [DE] Fed. Rep. of Germany ....... 3210708

[51] Int. Cl.$^4$ ............................................. C07C 67/39
[52] U.S. Cl. .................................. 560/208; 502/303; 502/326; 502/327
[58] Field of Search ....................... 560/208, 210, 238; 562/534; 502/303, 326, 327

[56] References Cited

U.S. PATENT DOCUMENTS

| | | | |
|---|---|---|---|
| 3,639,449 | 2/1972 | Kunugi ................. | 560/208 |
| 3,772,381 | 11/1973 | Nakamura et al. ............. | 560/208 |
| 3,959,354 | 5/1976 | Onoda et al. ............ | 560/208 |
| 4,249,019 | 2/1981 | Tamura et al. ............. | 560/208 |
| 4,356,316 | 10/1982 | Aoshima et al. ............. | 560/208 |

FOREIGN PATENT DOCUMENTS

| | | |
|---|---|---|
| 050942 | 3/1982 | Japan . |
| 8002829 | 11/1980 | Netherlands . |
| 2070601A | 9/1981 | United Kingdom . |

OTHER PUBLICATIONS

Haul, R. et al. *Chemie-Ing-Techn.* (1963) pp. 586–589.
Heslop, R. B. et al. *Inorganic Chemistry* (1967) at page 25, 3rd Ed. Elsevier Publishing Co.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

A catalyst which is free from alkali metal compounds and alkaline earth metal compounds, contains palladium and lead as active constituents and is supported on a carrier which contains two or more of the oxides ZnO, Al$_2$O$_3$, La$_2$O$_3$ and TiO$_2$, and the use of this catalyst for the preparation of methyl methacrylate from methacrolein, methanol and oxygen.

2 Claims, No Drawings

PREPARATION OF METHYL METHACRYLATE FROM METHACROLEIN

This is a continuation of application Ser. No. 473,601, filed Mar. 9, 1983, now abandoned.

The preparation of carboxylic acid esters from aldehydes and alcohols in the presence of oxygen, under the action of a catalyst, is a process which for some time past has been worked on in several quarters. A variety of catalysts has been proposed for this process, and amongst these the catalysts containing palladium as the active constituent have encountered interest. However, the catalysts of this type which have hitherto been disclosed have not yet fully met all user requirements, especially where they are employed for the preparation of esters of α,β-unsaturated aliphatic carboxylic acids, in particular methyl methacrylate (hereafter also referred to as MMA).

U.S. Pat. No. 3,772,381 discloses the use of metallic palladium as the catalyst for the reaction of α,β-unsaturated aliphatic aldehydes with lower monohydric primary or secondary alcohols and molecular oxygen to give esters of α,β-unsaturated aliphatic carboxylic acids, the catalyst being supported where appropriate, on a suitable carrier, especially alumina or silica. This catalyst has the disadvantage that it gives substantial amounts of by-products (27% by weight of methyl formate and 18% by weight of formaldehyde, based on methyl methacrylate). Moreover, only low conversions or only low selectivities are achieved, since the use of 3.58 moles of methacrolein/liter of catalyst per hour merely gives 0.11 mole of methyl methacrylate/liter of catalyst per hour (cf. loc.cit., Example 4).

U.S. Pat. No. 3,639,449 describes a very similar process for the preparation of carboxylic acid esters from aldehydes and/or alcohols by reaction with oxygen over a noble metal catalyst (for example palladium) at from 0° to 300° C. Here again, the limited usefulness of a pure palladium catalyst for the preparation of methyl methacrylate is revealed: Example 16, the only example which illustrates the preparation of methyl methacrylate from methanol and methacrolein over a catalyst consisting of 2% of Pd on active carbon, gives a methacrolein conversion of 17.3% with a selectivity of 56.1% as regards methyl methacrylate formation and 40.6% as regards propylene formation.

U.S. Pat. No. 4,249,019 discloses a catalyst for the preparation of carboxylic acid esters by reacting aldehydes with alcohols in the presence of oxygen at from 0° to 200° C., the catalyst containing (a) palladium, (b) an oxide, hydroxide, carbonate, nitrate or carboxylic acid salt of thallium or mercury and (c) an oxide, hydroxide, carbonate or carboxylic acid salt of an alkali metal or alkaline earth metal. It is true that this type of catalyst gives high selectivity of methyl methacrylate (90–95%), but the space-time yield, expressed as the productivity (g of MMA per g of Pd per h) leaves something to be desired. Moreover, it should be noted that the numerical data given for the productivity in Table 1 of the German Published Application were determined at a low conversion (cf. the last line of the Notes on the Table) and hence do not give a realistic picture of the productivity in relation to the total conversion; in fact, based on the total conversion to methyl methacrylate, the productivity is from 2 to 10.5.

We have found that the above shortcomings can be avoided by using a catalyst containing palladium and lead as active constituents, if these active constituents are supported on a carrier which contains two or more of the oxides ZnO, Al$_2$O$_3$, La$_2$O$_3$ and TiO$_2$ and if the catalyst is free from alkali metal compounds and alkaline earth metal compounds. The expression "free from alkali metal compounds and alkaline earth metal compounds" here means that neither the active catalyst constituents nor the carrier contain such compounds, though of course ubiquitous traces of alkali metal compounds and alkaline earth metal compounds can be left out of account. A catalyst which, based on its total weight, contains not more than 0.02% of an alkali metal or alkaline earth metal calculated as metal, conforms to the above requirements.

This means that certain otherwise commonly used carriers, such as calcium carbonate, kieselguhr and pumice cannot be employed, even as minor carrier constituents, for the catalyst according to the invention, because they contain alkali metal and/or alkaline earth metal. The same is true of most types of silica gel because of their substantial content of alkali metal. Carriers which essentially consist of ZnO and Al$_2$O$_3$, ZnO and La$_2$O$_3$, ZnO and TiO$_2$ or La$_2$O$_3$ and TiO$_2$ have proved very successful. Particularly good results are achieved with a carrier which has been formed by calcining the compound Zn$_6$Al$_2$(OH)$_{12}$(CO$_3$)$_3$ and which accordingly consists of ZnO and Al$_2$O$_3$, evidently in a particularly active structure. This carrier is obtained by coprecipitation from Zn(NO$_3$)$_2$ and Al(NO$_3$)$_3$ by means of sodium carbonate, the precipitate formed being filtered off, washed free from alkali, dried, calcined and pressed. The calcined product can then be either converted to extrudates or molded to form tablets. In the case of the preparation of the carrier described in Example 1, precipitation gives a quite specific Zn-Al hydroxide-carbonate, which is characterized by the lines encountered in the Guinier powder diagram.

The analytical composition corresponds to the empirical formula

$$Zn_6Al_2(OH)_{12}(CO_3)_3.$$

The catalyst according to the invention should have an inner surface area of from 10 to 60 m$^2$/g, determined by the BET method. This is achieved by using, for the preparation of the catalyst, a carrier whose BET surface area is roughly in the range of from 40 to 140 m$^2$/g. The method of determining the BET surface area is described by R. Haul and G. Dumbgen, Chem.-Ing.-Techn. 35, (1963), 586–589.

The catalyst according to the invention contains the palladium in the form of the metal, in an amount of from 0.1 to 10% by weight, preferably from 0.2 to 5% by weight, and more especially from 0.5 to 2% by weight, based on its total weight, i.e. including the carrier. The lead is present in the catalyst as metallic lead or as lead compounds, in an amount of from 0.1 to 20% by weight, preferably from 0.2 to 10% by weight, more especially from 0.2 to 2% by weight, calculated as metal and based on total weight. The catalyst can be prepared in a conventional manner, for example by treating the carrier first with an aqueous solution of a palladium salt, such as palladium chloride, and then with an aqueous solution of a lead salt, such as lead acetate, until the salts have been absorbed by the carrier, and carrying out a treatment with a reducing agent, such as hydrogen or formaldehyde, between or after the two impregnations, the finished carrier finally being dried.

The catalyst according to the invention is exceptionally suitable for the preparation of carboxylic acids, especially α,β-unsaturated carboxylic acids, from the corresponding aldehydes and alcohols in the presence of oxygen. It may be used particularly advantageously for the preparation of methyl methacrylate from methacrolein, methanol and oxygen at from 20° to 100° C. The reaction may be carried out in the gas phase or, preferably, in the liquid phase.

stirred for a further 15–60 minutes at 80° C. in an additional downstream vessel. The precipitate formed is filtered off, washed nitrate-free and spray-dried.

The formation of the compound $Zn_6Al_2(OH)_{12}(CO_3)_3$ can be demonstrated by means of the X-ray diagram of the carefully dried product. The compound is characterized by the following $Cu_K$ lines in the Guinier powder diagram.

| d(Å) | 6.8 | 4.55 | 3.32 | 2.8 | 2.62 | 2.44 | 1.75 | 1.66 | 1.52 | 1.31 |
|---|---|---|---|---|---|---|---|---|---|---|
| Intensity | very strong | very strong | strong | medium | strong | strong | medium | strong | strong | medium |

The catalyst according to the invention may be employed in batchwise or continuous operation. In other respects also, the preparation of methyl methacrylate using the catalyst according to the invention is carried out in a conventional manner, as with known catalysts. The molar ratio of alcohol to aldehyde should be from 200:1 to 1:1. The amount of catalyst used is of minor importance and can be from 0.2 to 10 times the weight of aldehyde, in batchwise operation. In continuous operation, the amount of catalyst may be from 100 to 1 part by weight per part by weight of aldehyde passed through the reaction chamber per hour.

If desired, the reaction may be carried out in a solvent which is inert towards the reactants.

The oxygen is employed as molecular oxygen in the pure form or in the form of a mixture with one or more other gases, such as nitrogen and carbon dioxide. Accordingly, for example, air may also be used. It has proved advantageous to employ the oxygen in more than the stoichiometric amount, preferably not less than 1.5 times the stoichiometric amount, for the reaction.

The reaction may be carried out under reduced, atmospheric or superatmospheric pressure. In general, operation under atmospheric pressure is preferred, for reasons of simplicity.

Using the catalyst according to the invention, high methacrolein conversions, of from 65 to 97%, are achieved even after short reaction times, and excellent selectivities in respect of methyl methacrylate, namely from 85 to 94%, are achieved. This, however, means a substantial increase in productivity (defined as g of methyl methacrylate per g of Pd per hour) compared to the catalysts known from the prior art discussed above.

EXAMPLE 1

Preparation of $Zn_6Al_2(OH)_{12}(CO_3)_3$ as a carrier intermediate

To precipitate the carrier intermediate, 2 solutions are required:

Solution 1:

54 moles of $Zn(NO_3)_2 \cdot 6 H_2O = 16.065$ kg and 18 moles of $Al(NO_3)_3 \cdot 9 H_2O = 6.750$ kg are dissolved in water and made up to 36 liters of solution, so that the solution formed is 2-molar.

Solution 2:

90 moles of technical-grade sodium carbonate = 9.54 kg are dissolved in water, so that 45 liters of a 2-molar solution are formed.

The two solutions are pumped simultaneously but separately into a stirred kettle and are combined at 80° C. and a pH of 7.0. The pH is kept constant during the precipitation by controlling the amount of solution. The catalyst carrier intermediate obtained as a precipitate is If the product is to be used as a catalyst carrier, special precautions on drying are not needed, since the product is in any case subsequently calcined to form a mixture of ZnO and $Al_2O_3$. The calcination temperature influences the inner surface area of the mixed oxide formed from the $Zn_6Al_2(OH)_{12}(CO_3)_3$. The BET surface area of the carrier formed is 135 m²/g if calcination is carried out at 350° C. and 74 m²/g if it is carried out at 650° C.

EXAMPLE 2

10 g of $Zn_6Al_2(OH)_{12}(CO_3)_3$ are calcined at 350° 50 ml of $H_2O$ are added, and the batch is mixed with a solution of 0.33 g of $PdCl_2$ in hydrochloric acid, while stirring. Stirring is continued until the supernatant solution is colorless and clear. The catalyst is filtered off, introduced, together with 100 ml of $H_2O$, into a flask, and reduced with $H_2$ for 4 hours at 60° C., while stirring. The catalyst is then filtered off and mixed with a solution of 0.33 g of $Pb(OAc)_2 \cdot 3 H_2O$ in 10 ml of $H_2O$, and the mixture is dried at 60°–70° C. and 20 mbar and is cooled under $N_2$. According to analysis, the catalyst contains 1.7% of Pd and 1.3% of Pb and has a BET surface area of 44 m²/g.

1.3 g of the catalyst thus prepared are introduced into a glass reactor (duck-shaped 250 ml shaking vessel) which is thermostatically kept at 30° C. and is connected to a gas burette, filled with oxygen, via tubing; a solution of 1 g of methacrolein in 19 g of methanol is added and the glass reactor is closed and shaken to start the reaction. After 1 hour, a sample is taken and analyzed by gas chromatography. It is found that 97% of the methacrolein employed have been converted, the selectivity with respect to methyl methacrylate (MMA) being 85%. The productivity is 50.3 g of MMA/g of Pd.h.

EXAMPLE 3

10 g of $Zn_6Al_{1.2}(OH)_2(CO_3)_3$ are calcined at 600° 50 ml of $H_2O$ are added, and the batch is mixed with a solution of 0.33 g of $PdCl_2$ in hydrochloric acid, while stirring. Stirring is continued until the supernatant solution is colorless and clear. The catalyst is filtered off, suspended in 100 ml of $H_2O$ and reduced for 2 hours by adding 3.12 ml of a 30% strength formaldehyde solution at 60° C., with stirring. The catalyst is then filtered off under $N_2$ and mixed with a solution of 0.33 g of $Pb(OAc)_2 \cdot 3H_2O$ in 40 ml of $H_2O$, the mixture is dried at 60°–70° C. and 20 mbar pressure, and the residue is cooled under $N_2$. According to analysis, the catalyst contains 1.8% of Pd and 1.4% of Pb, and has a BET surface area of 28 m²/g.

4 g of the catalyst thus prepared are introduced into a glass reactor (duck-shaped 1,000 ml shaking vessel)

which is thermostatically kept at 40° C. and is connected to a gas burette, filled with oxygen, via tubing; a solution of 2 g of methacrolein in 48 g of methanol is added and the glass reactor is closed and shaken to start the reaction. After half an hour, a sample is taken and analyzed by gas chromatography. It is found that 84.3% of the methacrolein employed have been converted, the selectivity with respect to methyl methacrylate (MMA) being 92.1%. The productivity is 61.6 g of MMA/g of Pd.h.

EXAMPLE 4

A catalyst is prepared by heating a mixture of 4.5 g of $TiO_2$-P25 (Degussa), 4.5 g of ZnO (MeFck), 1.0 g of $La_2O_3$ and 0.2 g of graphite at 600° C. for 20 hours and then charging the product with Pd and Pb as described in Example 3. According to analysis, the catalyst contains 1.8% of Pd and 1.4% of Pb and has a BET surface area of 24 $m^2/g$.

The reaction of methacrolein with oxygen and methanol, using this catalyst, is carried out as described in Example 3. After 1 hour, a sample is taken and analyzed by gas chromatography. It is found that 80.5% of the methacrolein employed have been converted, the selectivity with respect to methyl methacrylate being 93.9%. The productivity is 29.9 g of MMA/g of Pd.h.

EXAMPLE 5

10 g of $Zn_6Al_2(OH)_{12}(CO_3)_3$ are calcined at 700° C. and are charged with Pd and Pb, and reduced, as described in Example 3. According to analysis, the catalyst contains 1.7% of Pd and 1.3% of Pb and has a BET surface area of 17 $m^2/g$.

The reaction of methacrolein with oxygen, using this catalyst, is carried out as described in Example 3. After half an hour's duration of the experiment, a sample is taken and analyzed by gas chromatography. It is found that 65% of the methacrolein employed have been converted, the selectivity with respect to methyl methacrylate being 94.2%. The productivity is 51.5 g of MMA/g of Pd.h.

EXAMPLE 6

A catalyst is prepared by heating a mixture of 4.5 g of $TiO_2$-P25 (Degussa), 4.5 g of ZnO (Merck) and 0.2 g of graphite at 600° C. for 20 hours and then charging the product with Pd and Pb as described in Example 3. According to analysis, the catalyst contains 1.8% of Pd and 1.4% of Pb and has a BET surface area of 38 $m^2/g$.

The reaction of methacrolein with oxygen and methanol, using this catalyst, is carried out as described in Example 3. After 1 hour's duration of the experiment, a sample is taken and analyzed by gas chromatography. It is found that 67.5% of the methacrolein employed have been converted, the selectivity with respect to methyl methacrylate being 89%. The productivity is 23.5 g of MMA/g of Pd.h.

EXAMPLE 7

100 g of $TiO_2$-P5 (Degussa) and 100 g of ZnO (Merck) are suspended in 3 liters of $H_2O$ and the mixture is refluxed for 12 hours. When it has cooled, the catalyst carrier is filtered off, converted to extrudates of 2 mm diameter, and heated for 20 hours at 600° C. 100 g of these extrudates are treated with 200 g of an aqueous hydrochloric solution of $PdCl_2$, containing 0.35% of Pd, in a glass tube, by circulating the solution through the tube until the solution turns colorless (which requires about 2–4 hours). Thereafter, 0.82 g of $Pb(OAc)_2.3 H_2O$ is added to the solution and circulation is continued for 2 hours. 11.69 g of a 30% strength $CH_2O$ solution are then added and the catalyst is reduced for 4 hours at 60° C. According to analysis, the catalyst contains 0.52% of Pd and 0.44% of Pb and has a BET surface area of 15 $m^2/g$.

100 g of this catalyst are introduced into a reactor consisting of a thermostatically controlled glass tube of 1 m length and 1.1 cm diameter.

The reactor is kept at 40° C. and per hour 2 liters of oxygen are introduced at the bottom and 10 g of a 10% strength solution of methacrolein in methanol are introduced from the top. The reaction solution is circulated at a frequency of 2 liters/hour so that the reaction is effected in a continuous flow system. After 48 hours, the methacrolein conversion is 84.5% and the selectivity with respect to methyl methacrylate is 83.7%; after 300 hours the conversion is 83.5% and the selectivity is 85.9%. The productivity is 2.0 g of MMA/g of Pd.h.

EXAMPLE 8

200 g of $Zn_6Al_2(OH)_{12}(CO_3)_3$ are converted to extrudates of 3 mm diameter and then calcined for 6 hours at 350° C. 100 g of these extrudates are treated with a solution of 3.3 g of $PdC_2$ in 500 ml of $H_2O$, containing hydrochloric acid, by stirring the mixture from time to time until the supernatant solution is colorless and clear. The water is decanted and the catalyst residue is then reduced with 500 ml of a 5% strength formaldehyde solution for 16 hours at 60° C. The solution is removed and the catalyst is treated with a solution of 3.3 g of $Pb(OAc)_2.3 H_2O$ in 300 ml of $H_2O$ for 4 hours. Thereafter, the catalyst is dried at 60° C. under $N_2$. According to analysis, the catalyst contains 1.3% of Pd and 0.85% of Pb and has a BET surface area of 24 $m^2/g$.

26 g of this catalyst are introduced into a thermostatically controlled reaction tube of 0.3 m length and 1.1 cm diameter. The reaction tube is kept at 40° C. and 16 g per hour of a 10% strength solution of methacrolein in methanol, and 1.3 liters per hour of oxygen are introduced at the bottom. After 7 hours, the methacrolein conversion is 79.9% and the selectivity with respect to methyl methacrylate is 92.2%; after 300 hours the conversion is 78.9% and the selectivity is 89.7%. The productivity is 4.8 g of MMA/g of Pd.h.

EXAMPLE 9

A catalyst is prepared by heating a mixture of 6 g of $La_2O_3$, 4 g of $TiO_2$-P25 (Degussa) and 0.2 g of graphite at 600° C. for 20 hours and then charging the product with Pd and Pb as described in Example 3. According to analysis, the catalyst contains 1.8% of Pd and 1.2% of Pb and has a BET surface area of 13 $m^2/g$.

The reaction of methacrolein with oxygen and methanol, using this catalyst, is carried out as described in Example 3. After 1 hour, a sample is taken and analyzed by gas chromatography. It is found that 65% of the methacrolein employed have been converted, the selectivity with respect to methyl methacrylate being 91%. The productivity is 23.5 g of MMA/g of Pd.h.

We claim:

1. A process for the preparation of methyl methacrylate by reacting methacrolein, methanol and oxygen at from 20° to 100° C. over a catalyst for the preparation of carboxylic acid esters from aldehydes and alcohols in the presence of oxygen, said catalyst containing palladium and lead as active constituents, wherein (a) the active constituents are supported on a carrier which contains two or more of oxides selected from the group consisting of ZnO, $Al_2O_3$, $La_2O_3$ and $TiO_2$, and
(b) said catalyst is free from alkali metal compounds and alkaline earth metal compounds.

2. A process for the preparation of methyl methacrylate by reacting methacrolein, methanol and oxygen at from 20° to 100° C. over a catalyst as in claim 1, wherein the active constituents are supported on a carrier which is formed by calcining the compound $Zn_6Al_2(OH)_{12}(CO_3)_3$.

* * * * *